(12) United States Patent
Sato

(10) Patent No.: US 8,808,184 B2
(45) Date of Patent: Aug. 19, 2014

(54) ULTRASOUND DIAGNOSTIC APPARATUS

(75) Inventor: Tomoo Sato, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 548 days.

(21) Appl. No.: 13/013,444

(22) Filed: Jan. 25, 2011

(65) Prior Publication Data

US 2011/0245677 A1 Oct. 6, 2011

(30) Foreign Application Priority Data

Mar. 31, 2010 (JP) .................................. 2010-080676

(51) Int. Cl.
*A61B 8/00* (2006.01)
(52) U.S. Cl.
USPC ........................................ 600/437; 600/459
(58) Field of Classification Search
None
See application file for complete search history.

(56) References Cited

U.S. PATENT DOCUMENTS

| | | | | |
|---|---|---|---|---|
| 5,623,928 | A * | 4/1997 | Wright et al. .................. | 600/447 |
| 2005/0148878 | A1 * | 7/2005 | Phelps et al. .................. | 600/459 |
| 2008/0114255 | A1 * | 5/2008 | Schwartz et al. .............. | 600/474 |
| 2010/0174194 | A1 * | 7/2010 | Chiang et al. ................. | 600/447 |

FOREIGN PATENT DOCUMENTS

| | | |
|---|---|---|
| JP | 2005-279130 A | 10/2005 |
| JP | 2007-209700 A | 8/2007 |
| JP | 2007229015 A | 9/2007 |

OTHER PUBLICATIONS

Notification of Reasons for Refusal, dispatched Sep. 17, 2013, issued in corresponding JP Application No. 2010-080676, 5 pages in English and Japanese.

* cited by examiner

*Primary Examiner* — James Kish
(74) *Attorney, Agent, or Firm* — Sughrue Mion, PLLC

(57) ABSTRACT

An ultrasound diagnostic apparatus comprises: an ultrasound probe having a plurality of ultrasound transducers; an apparatus body which supplies analog drive signals to the ultrasound transducers and generates ultrasound images based on reception signals output from the ultrasound transducers; and a connection cable which connects the ultrasound probe and the apparatus body, the ultrasound probe comprising: a plurality of receiving circuits, each including a preamp which amplifies the reception signal output from one of the ultrasound transducers and an A/D converter which converts the amplified reception signal; and a time division unit which controls output of the reception signal to the apparatus body such that the drive signal supplied from the apparatus body and the reception signal output to the apparatus body after being converted to a digital signal by the receiving circuit are mutually time-divided and sent via the connection cable.

7 Claims, 7 Drawing Sheets

ULTRASOUND DIAGNOSTIC APPARATUS

BACKGROUND OF THE INVENTION

The present invention relates to an ultrasound diagnostic apparatus, particularly to an ultrasound diagnostic apparatus which transmits an ultrasonic beam from an ultrasound probe toward a subject, receives ultrasonic echoes reflected by the subject by an ultrasound probe and sends that reception signal to an apparatus body, wherein the apparatus body and ultrasound probe are connected by a connection cable.

In recent years, ultrasound diagnostic apparatus that use ultrasound images have been put to use in the medical field. In general, this type of ultrasound diagnostic apparatus has an ultrasound probe equipped with a plurality of ultrasound transducers arranged in an array, and an apparatus body connected to the ultrasound probe via a connection cable. It transmits ultrasonic waves from the ultrasound probe toward a subject, receives the ultrasonic echoes from the subject by the ultrasound probe, and generates an ultrasound image by digitally processing the reception signals in the apparatus body.

Here, in the connection cable which connects the ultrasound probe and the apparatus body, the reception signals obtained by the ultrasound transducers of the ultrasound probe are sent from the ultrasound probe to the apparatus body, and additionally, drive signals for driving the ultrasound transducers are sent from the apparatus body to the ultrasound probe. For this reason, transmission signal wires for sending the drive signals and reception signal wires for sending the reception signals corresponding to the plurality of ultrasound transducers arranged in the ultrasound probe are required, and as the number of ultrasound transducers increases, the number of signal wires in the connection cable also increases.

When the number of signal wires increases, problems occur in that the connection cable becomes thick and heavy, and maneuverability of the ultrasound probe decreases.

If each signal wire of the connection cable is made lighter and narrower in order to counteract these problems, it causes problems in that mixing in of external noise and attenuation due to the resistance of the signal wires occur, and detection precision of the reception signal is markedly reduced.

Thus, in JP 2005-279130 A, for example, a technique was proposed wherein the drive signals and the reception signals for the ultrasound transducers are sent by few signal wires, regardless of the number of ultrasound transducers, by connecting a delay circuit to each of the plurality of ultrasound transducers in the ultrasound probe and sending signals that are divided over time corresponding to the plurality of ultrasound transducers.

Also, in JP 2007-209700 A, an apparatus was proposed wherein the number of signal wires of the connection cable is reduced by actively switching between transmission of the drive signals and reception of the reception signals via a switch, and detection precision of the reception signals is improved by incorporating a preamp in the ultrasound probe and amplifying the reception signals.

However, in the ultrasound diagnostic apparatus according to JP 2005-279130 A, a certain delay is provided to both the high-voltage drive signals for driving the ultrasound transducers and to the tiny reception signals, but in general, the time precision of analog delay wires is low, and it is difficult to delay drive signals which are more than 100 V at maximum with high precision.

Also, realizing the apparatus disclosed in JP 2007-209700 A is difficult because a practical electronic switch that can operate at a high speed of about 1 μs while having a breakdown voltage of 100 V or above has not yet been developed.

SUMMARY OF THE INVENTION

The present invention was developed to resolve these problems of the past, and its objective is to provide an ultrasound diagnostic apparatus which reduces the thickness and weight of the connection cable which connects the ultrasound probe and apparatus body, while being able to detect reception signals with high precision.

An ultrasound diagnostic apparatus according to the present invention comprises:

an ultrasound probe having a plurality of ultrasound transducers arranged in an array;

an apparatus body which supplies analog drive signals to the plurality of ultrasound transducers of said ultrasound probe to transmit an ultrasonic beam toward a subject, and generates ultrasound images based on reception signals output from said plurality of ultrasound transducers which received ultrasonic echoes due to the subject; and a connection cable which connects said ultrasound probe and said apparatus body, said ultrasound probe comprising:

a plurality of receiving circuits, each including a preamp which amplifies the reception signal output from one of said plurality of ultrasound transducers and an A/D converter which converts the reception signal amplified by said preamp to a digital signal; and time division means which controls output of said reception signal to said apparatus body such that said drive signal supplied from said apparatus body and said reception signal output to said apparatus body after being converted to a digital signal by said receiving circuit are mutually time-divided and sent via said connection cable.

DETAILED DESCRIPTION OF THE INVENTION

Embodiments of the present invention will be described below based on the appended drawings.

Embodiment 1

Figure 1:
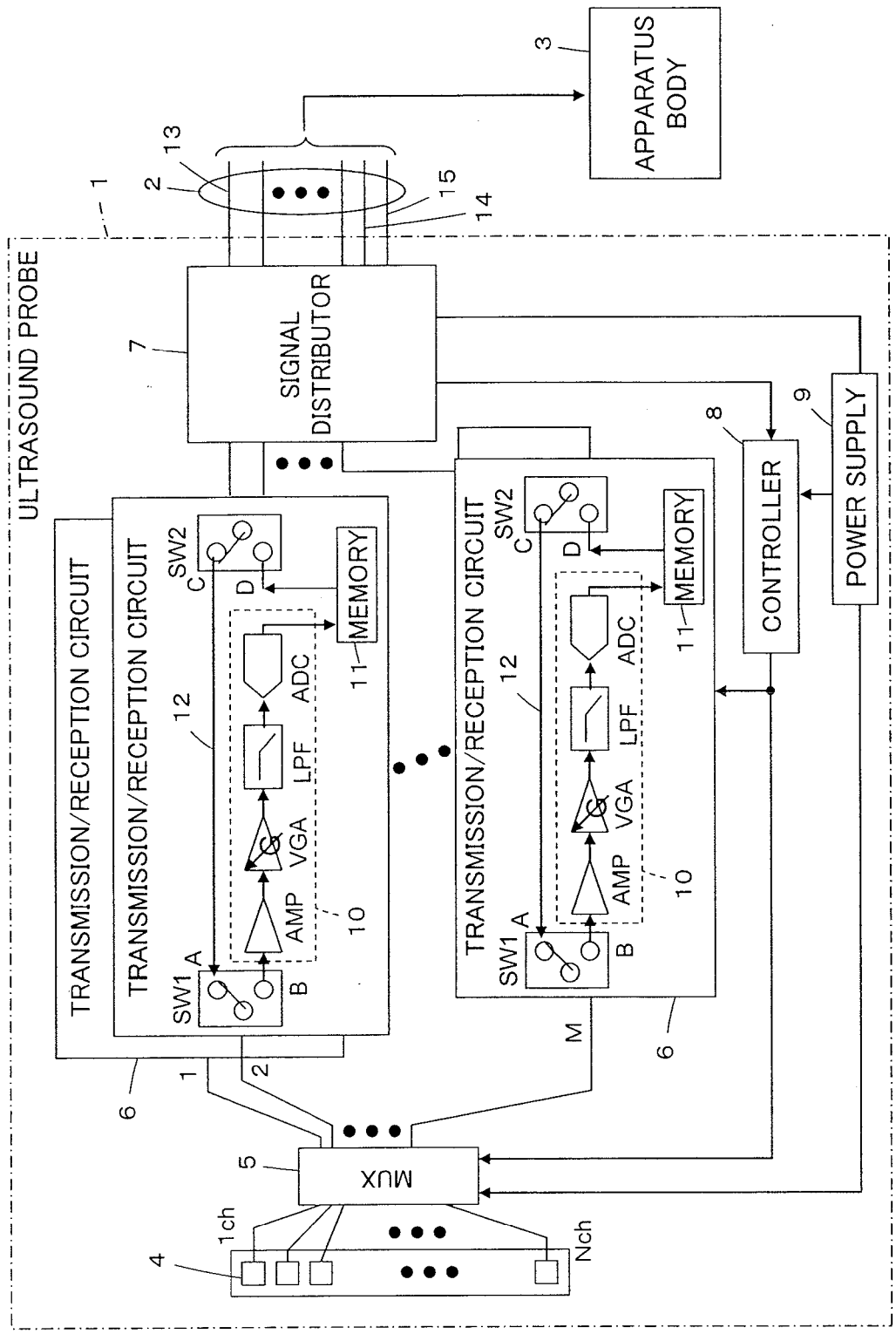
FIG. 1 is a block diagram illustrating a configuration of an ultrasound diagnostic system according to embodiment 1 of the invention.

FIG. 1 illustrates a configuration of an ultrasound diagnostic apparatus according to embodiment 1 of the invention. The ultrasound diagnostic apparatus comprises an ultrasound probe 1, and an apparatus body 3 which is electrically connected to the ultrasound probe 1 via a connection cable 2.

The ultrasound probe 1 has N ultrasound transducers 4 of a 1st channel through an Nth channel arranged in an array. M transmission/reception circuits 6 are connected to these ultrasound transducers 4 via a multiplexer 5, and a signal distributor 7 is connected to these M transmission/reception circuits 6. Additionally, a controller 8 for controlling the operation of the multiplexer 5 and the transmission/reception circuits 6 is connected to the signal distributor 7, and a power supply 9 which supplies power to the multiplexer 5, the transmission/reception circuits 6 and the controller 8 is also connected to the signal distributor 7.

Each transmission/reception circuit 6 has a receiving circuit 10, in which a preamp AMP and a variable gain amp VGA which amplify a reception signal output from the ultrasound transducer 4 due to a reception of an ultrasound echo, a low pass filter LPF which removes high-frequency components not used in signal detection from the reception signal, and an A/D converter ADC which converts the reception signal to a digital signal are connected in series in that order. Also, each transmission/reception circuit 6 has a memory 11 connected in series to the receiving circuit 10, and has a transmission signal wire 12 arranged in parallel to the receiving circuit 10 and the memory 11. The memory 11 is for temporarily storing reception signals that were converted to digital signals by the A/D converter ADC of the receiving circuit 10.

In addition, a switch SW1 which selectively connects either the receiving circuit 10 or the transmission signal wire 12 to the multiplexer 5, and a switch SW2 which selectively connects either the memory 11 or the transmission signal wire 12 to the signal distributor 7, are arranged in each transmission/reception circuit 6. The switch SW1 is a passive switch which automatically operates based on the potential of the transmission signal wire 12. The switch SW1 connects the transmission signal wire 12 to the multiplexer 5 when the potential of the transmission signal wire 12 exceeds a preset threshold value due to supply of a drive signal from the apparatus body 3, and connects the receiving circuit 10 to the multiplexer 5 when the potential of the transmission signal wire 12 is equal to or lower than the threshold value with no drive signal being supplied. On the other hand, the switch SW2 is a general-purpose active switch which operates based on an SW2 control signal input from the controller 8. These switches SW1 and SW2 constitute switching means which connects or blocks the connection cable 2 and the receiving circuit 10 to or from each other.

The connection cable 2 is connected to the signal distributor 7 of the ultrasound probe 1. The connection cable 2 has m signal wires 13 for sending drive signals and reception signals, a control wire 14 and a power supply wire 15. The m signal wires 13 of the connection cable 2 are connected to the M transmission/reception circuits 6 via the signal distributor 7, and the control wire 14 and the power supply wire 15 are connected to the controller 8 and the power supply 9, respectively, via the signal distributor 7.

Note that the number M of the transmission/reception circuits 6 is the same or less than the number N of the ultrasound transducers 4, and the number m of the signal wires 13 of the connection cable 2 is the same or less than the number M of the transmission/reception circuits 6.

Also, note that the apparatus body 3 supplies analog high-voltage drive signals to the ultrasound transducers 4 of the ultrasound probe 1 via the signal wires 13 of the connection cable 2, and generates and displays an ultrasound image based on the reception signals input from the ultrasound probe 1 via the signal wires 13 of the connection cable 2.

Figure 2:
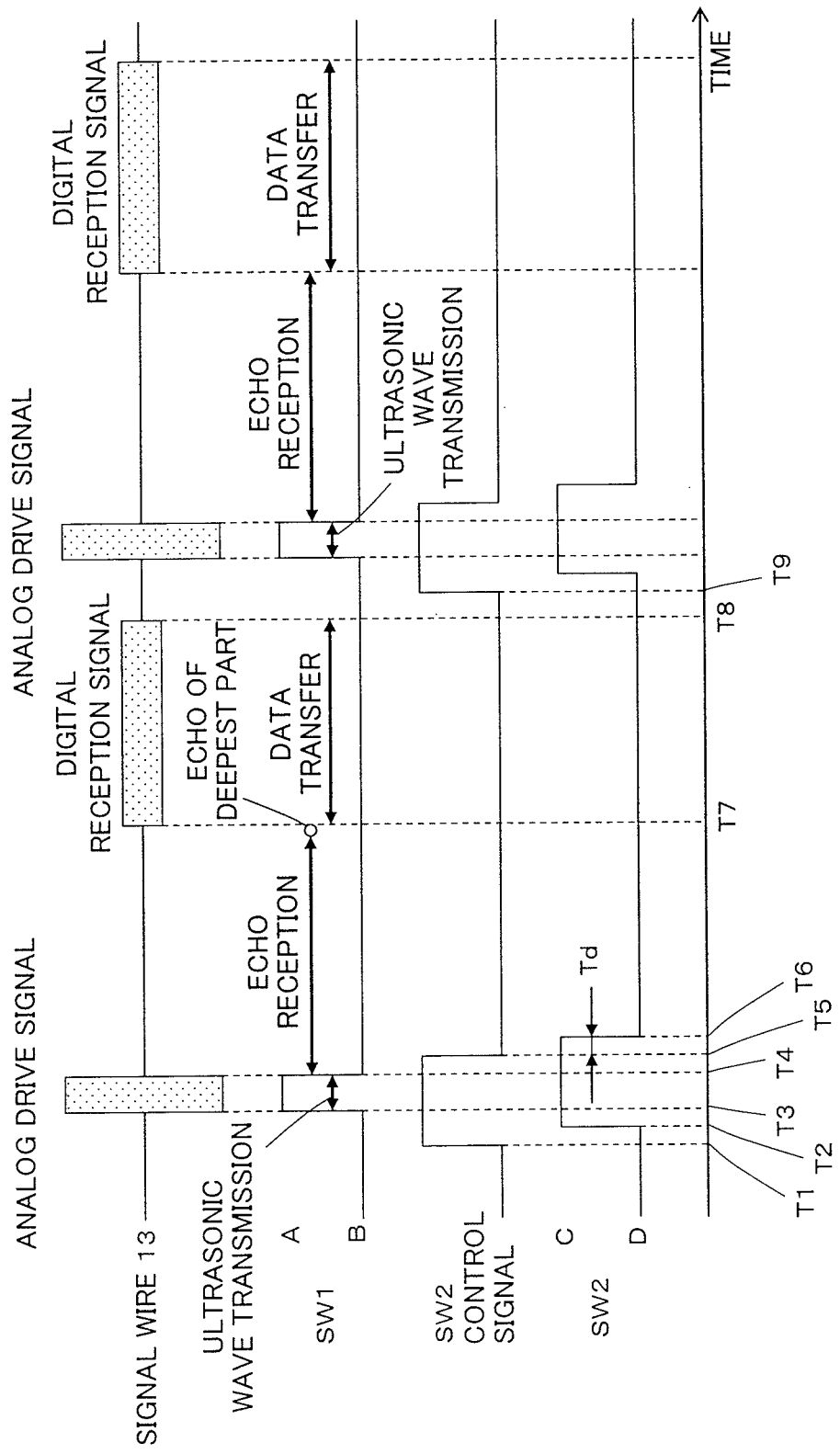
FIG. 2 is a timing chart illustrating an operation of embodiment 1.

Next, the operation of embodiment 1 will be described referring to the timing chart of FIG. 2.

First, a command is sent from the apparatus body 3 to the controller 8 of the ultrasound probe 1 via the control wire 14 of the connection cable 2, and at time T1, the controller 8 outputs an SW2 control signal to the switch SW2 of the 1st transmission/reception circuit 6 to connect the signal distributor 7 and transmission signal wire 12, and connects the 1st transmission/reception circuit 6 and the ultrasound transducer 4 of the 1st channel by means of the multiplexer 5. By means of the SW2 control signal, the switch SW2 operates at time T2 when a response time Td required by the switch SW2 has elapsed, and the transmission signal wire 12 of the 1st transmission/reception circuit 6 is thereby connected to the signal distributor 7.

After that, at time T3, when an analog high-voltage drive signal is supplied from the apparatus body 3 to the ultrasound probe 1 via the 1st signal wire 13 of the connection cable 2, this drive signal is sent from the switch SW2 of the 1st transmission/reception circuit 6 to the transmission signal wire 12 via the signal distributor 7. Since the potential of the transmission signal wire 12 exceeds the threshold value due to the sending of the drive signal, the passive switch SW1 is automatically switched such that it connects the transmission signal wire 12 to the multiplexer 5.

In this way, the drive signal passes through the transmission signal wire 12 of the 1st transmission/reception circuit 6, and is supplied to the ultrasound transducer 4 of the 1st channel via the multiplexer 5. As a result, an ultrasonic wave is transmitted from the ultrasound transducer 4 of the 1st channel toward the subject (not shown).

At time T4, when the supply of the drive signal ends, the passive switch SW1 is automatically switched such that it connects the receiving circuit 10 and the multiplexer 5, since the potential of the transmission signal wire 12 of the 1st transmission/reception circuit 6 is equal to or below the threshold value. For this reason, the reception signal output from the ultrasound transducer 4 of the 1st channel which received an ultrasonic echo by the subject is input into the receiving circuit 10 of the 1st transmission/reception circuit 6 via the multiplexer 5. The reception signal thus input is amplified by the preamp AMP and variable gain amp VGA, removed of high-frequency components by the low pass filter LPF, converted to a digital signal by the A/D converter ADC, and then stored in the memory 11. In this way, ultrasonic echoes are received starting at time T4, and the reception signals output from the ultrasound transducer 4 of the 1st channel are processed in succession by the receiving circuit 10 and stored in the memory 11.

At time T5, when a certain time has elapsed after time T4 at which the supply of drive signals ended, based on a command from the apparatus body 3, an SW2 control signal is output to the switch SW2 of the 1st transmission/reception circuit 6 via the controller 8 to connect the signal distributor 7 and the memory 11. As a result, the switch SW2 operates at time T6 when a response time Td required by the switch SW2 has elapsed, and the memory 11 of the 1st transmission/reception circuit 6 is thereby connected to the signal distributor 7.

Although reception of ultrasonic echoes continues during switching of the switch SW2, the reception of ultrasonic echoes ends when an echo has been received from the deepest part of the subject, and at time T7, based on a command from the apparatus body 3, the digital reception signals which have been stored in the memory 11 of the 1st transmission/reception circuit 6 since time T4 are collected via the controller 8, and are sent to the apparatus body 3 via the switch SW2, the signal distributor 7 and the 1st signal wire 13 of the connection cable 2. That is, the analog drive signals and the digital reception signals are mutually time-divided and sent via a common signal wire 13.

In this way, transmission of ultrasonic waves and reception of ultrasonic echoes by the ultrasound transducer 4 of the 1st channel is completed at time T8.

After that, at time T9, transmission of ultrasonic waves and reception of ultrasonic echoes by the ultrasound transducer 4 of the next channel begin.

Transmission of ultrasonic waves and reception of ultrasonic echoes using each of the m signal wires 13 of the connection cable 2 can be performed as those for the 1st signal wire 13 of the connection cable 2 described above.

When reception signals have been input by all of the ultrasound transducers 4 of the 1st channel through the Nth channel, the apparatus body 3 generates an ultrasound image by processing those reception signals, and displays it on a display monitor or the like.

Figure 3:
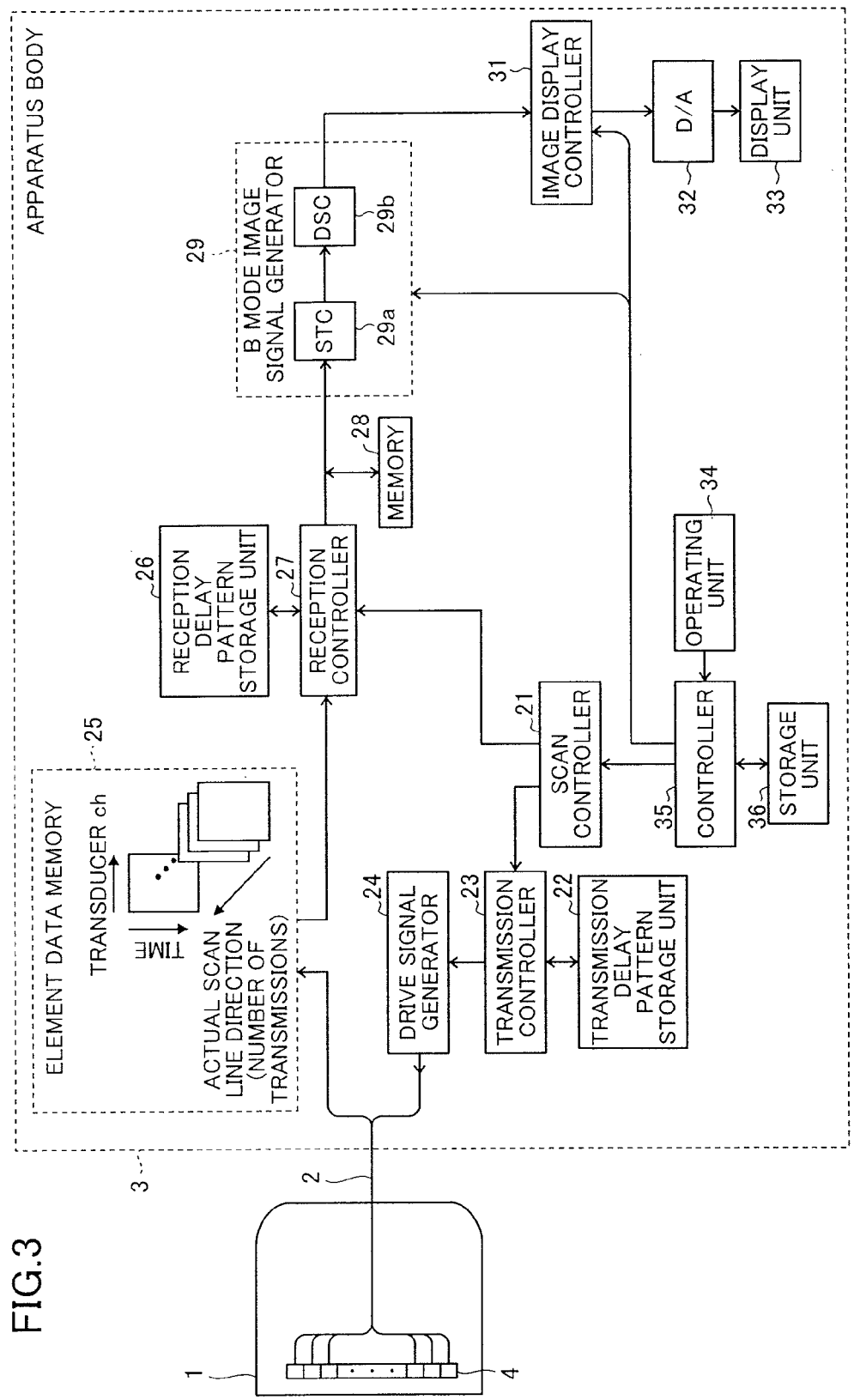
FIG. 3 is a block diagram illustrating an internal structure of the apparatus body in embodiment 1.

An example of the internal configuration of the apparatus body 3 is shown in FIG. 3.

The apparatus body 3 comprises a scan controller 21, a transmission delay pattern storage unit 22, a transmission controller 23, a drive signal generator 24, an element data memory 25, a reception delay pattern storage unit 26, a reception controller 27, a memory 28, a B mode image signal generator 29, an image display controller 31, a D/A converter 32, a display unit 33, an operating unit 34, a controller 35 and a storage unit 36.

The scan controller 21 sets a transmission direction of an ultrasonic beam and a reception direction of an ultrasonic echo in succession. The transmission delay pattern storage unit 22 stores a plurality of transmission delay patterns used when forming an ultrasonic beam. The transmission controller 23 selects one pattern from the plurality of delay patterns stored in the transmission delay pattern storage unit 22 in accordance with the transmission direction set in the scan controller 21, and based on that pattern, it sets the delay time provided to a drive signal of each of the plurality of ultrasound transducers 4. Or, the transmission controller 23 may set the delay time such that ultrasonic waves transmitted all at once from the plurality of ultrasound transducers 4 reach the entire imaged region of the subject.

The drive signal generator 24 is constructed from a plurality of pulsars, for example, corresponding to the plurality of ultrasound transducers 4. According to the delay time set by the transmission controller 23, the drive signal generator 24 supplies a plurality of drive signals to the ultrasound probe 1 such that the ultrasonic waves transmitted from the plurality of ultrasound transducers 4 form an ultrasonic beam, or, the drive signal generator 24 supplies a plurality of drive signals to the ultrasound probe 1 such that the ultrasonic waves transmitted all at once from the plurality of ultrasound transducers 4 reach the entire imaged region of the subject.

Digital reception signals from the ultrasound probe 1 are stored in the element data memory 25. The element data memory 25 stores the reception signal of each point in time corresponding to the transducer 4 of each channel of the ultrasound probe 1, for each time an ultrasonic wave is transmitted.

The reception delay pattern storage unit 26 stores a plurality of reception delay patterns used when a focusing process is performed on the plurality of reception signals output from the plurality of ultrasound transducers 4. The reception controller 27 selects one pattern from the plurality of reception delay patterns stored in the reception delay pattern storage unit 26 based on the reception direction set in the scan controller 21, and based on that reception delay pattern, performs the reception focusing process by providing delays in the plurality of reception signals stored in the element data memory 25, and adding them up. Also, a transmission focusing process may be performed based on the reception signals. Through this focusing process, a sound ray signal in which the focal points of the ultrasonic echoes are made to converge is generated. In addition, the reception controller 27 performs an envelope detection processing on the generated sound ray signal.

The sound ray signal generated by the reception controller 27 is supplied to the memory 28 as well as the B mode image signal generator 29. The B mode image signal generator 29 comprises an STC (sensitivity time controller) 29a and a DSC (digital scan converter) 29b. Based on the sound ray signal supplied from the reception controller 27, the B mode image signal generator 29 generates a B mode image signal, which is tomographic image information pertaining to the tissue in the subject. Also, in freeze mode, B mode image signals are generated based on the sound ray signals stored in the memory 28.

For the sound ray signals supplied from the reception controller 27 or memory 28, the STC 29a corrects attenuation due to distance in accordance with the depth of the reflection location of the ultrasound wave. The DSC 29b performs raster conversion of the sound ray signal corrected by the STC 29a into an image signal by the scanning method of an ordinary television signal, and then generates a B mode image signal by performing the required image processing such as contrast processing.

The image display controller 31 generates an image signal which represents the ultrasound image of the subject based on the B mode image signal generated by the B mode image signal generator 29. The D/A converter 32 converts the digital image signal output from the image display controller 31 to an analog image signal. The display unit 33 comprises a display apparatus such as an LCD, for example, and displays an ultrasound image of the subject based on the analog image signal.

The controller 35 controls the scan controller 21, the B mode image signal generator 29, the image display controller 31 and so forth according to operations performed by an operator using the operating unit 34. The scan controller 21, the transmission controller 23, the reception controller 27, the B mode image signal generator 29, the image display controller 31 and the controller 35 are constructed from a CPU and software (program), but they can also be constructed from digital circuits and analog circuits. The aforementioned software (program) is stored in the storage unit 36. A recording medium in the storage unit 36 may be a built-in hard disk, or a flexible disk, MO, MT, RAM, CD-ROM, DVD-ROM or the like may be used.

As described above, according to embodiment 1, the N ultrasound transducers 4 and the M transmission/reception circuits 6 are connected via a multiplexer 5, and the M transmission/reception circuits 6 and m signal wires 13 are connected via the signal distributor 7, and switching between the receiving circuit 10 and the transmission signal wire 12 is performed by two switches SW1 and SW2 in each transmission/reception circuit 6. Therefore, drive signals and reception signals can be sent using a number of signal wires 13 which is less than the number of ultrasound transducers 4.

Also, in each transmission/reception circuit 6, the reception signals from the ultrasound transducer 4 are temporarily stored in the memory 11, and after the switch SW2 is switched, the reception signals in the memory 11 are collected and transferred to the apparatus body 3, and for this reason, all of the reception signals can be detected by the apparatus body 3 without losing some of the reception signals, even if a general-purpose active switch having a certain response time Td is used as the switch SW2.

In addition, in each receiving circuit 10, the reception signals output from the ultrasound transducer 4 are amplified by the preamp AMP and the variable gain amp VGA, converted to digital signals by the A/D converter ADC and then stored in the memory 11, and thereafter transferred to the apparatus body 3. As a result, a mixing of noise in data transfer is reduced and a clearer ultrasound image can be obtained, even if shielded coaxial cables are not used for the signal wires 13 of the connection cable 2.

Embodiment 2

Figure 4:
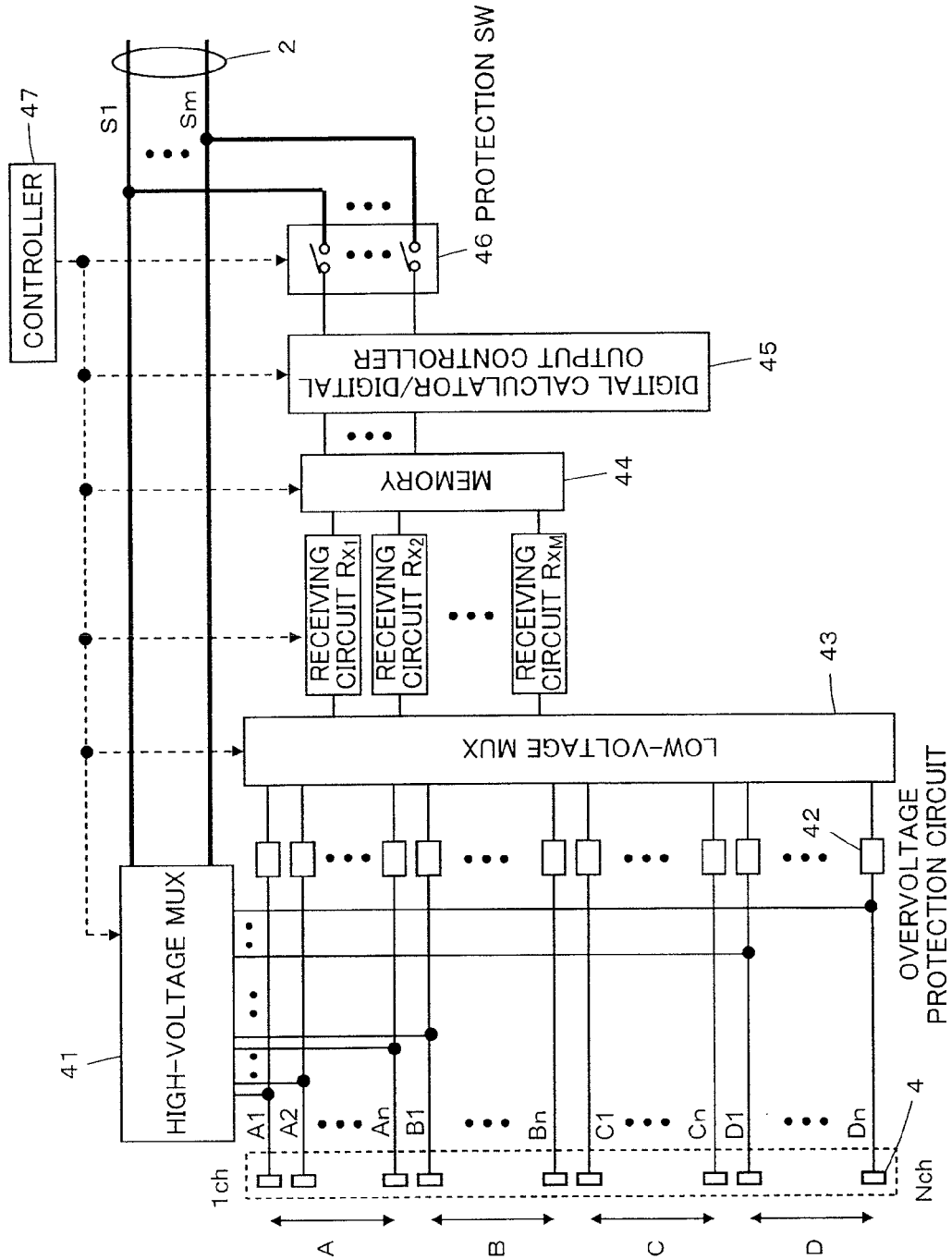
FIG. 4 is a block diagram illustrating an internal structure of an ultrasound probe used in embodiment 2.

FIG. 4 illustrates the internal structure of an ultrasound probe used in an ultrasound diagnostic apparatus according to embodiment 2.

Here, m signal wires S1-Sm of the connection cable 2 are connected to N ultrasound transducers 4 of the 1st to Nth channels arranged in an array via a high-voltage multiplexer 41.

Also, a low-voltage multiplexer 43 is connected to the N ultrasound transducers 4 via respective overvoltage protection circuits 42, and M receiving circuits Rx1-RxM are connected to this low-voltage multiplexer 43. Each of the receiving circuits Rx1-RxM, similar to the receiving circuit 10 in embodiment 1 shown in FIG. 1, has a preamp AMP and a variable gain amp VGA which amplify a reception signal, a low pass filter LPF which removes high-frequency components not used in signal detection from the reception signal, and an A/D converter ADC which converts the reception signal to a digital signal, which are connected in series in that order.

A common memory 44 is connected to the M receiving circuits Rx1-RxM, and a digital calculator/digital output controller 45 is connected to this memory 44. Additionally, the m signal wires S1-Sm of the connection cable 2 are connected to the digital calculator/digital output controller 45 via a protection switch 46 made up of m general-purpose active switches.

Also, a controller 47 is connected to the high-voltage multiplexer 41, the low-voltage multiplexer 43, the M receiving circuits R1-RM, the memory 44, the digital calculator/digital output controller 45 and the protection switch 46.

In embodiment 2, for convenience, the N ultrasound transducers 4 are divided into four groups A-D, made up of n ultrasound transducers A1-An, B1-Bn, C1-Cn and D1-Dn, respectively. Also, the number n of ultrasound transducers in each of groups A-D is equal to the number m of signal wires S1-Sm of the connection cable 2, and the number M of receiving circuits Rx1-RxM is set such that it is twice the number m of signal wires S1-Sm of the connection cable 2.

Figure 5:
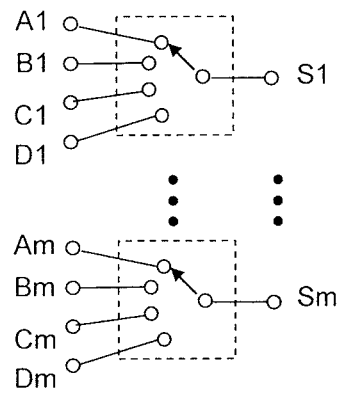
FIG. 5 is a drawing schematically illustrating a high-voltage multiplexer used in the ultrasound probe of embodiment 2.

As shown in FIG. 5, the high-voltage multiplexer 41 is a 4:1 multiplexer which selectively connects the signals wires S1-Sm to the respective four ultrasound transducers of groups A-D. For example, the 1st signal wire S1 is connected to either the 1st ultrasound transducer A1 of group A, the 1st ultrasound transducer B1 of group B, the 1st ultrasound transducer C1 of group C, or the 1st ultrasound transducer D1 of group D.

Figure 6:
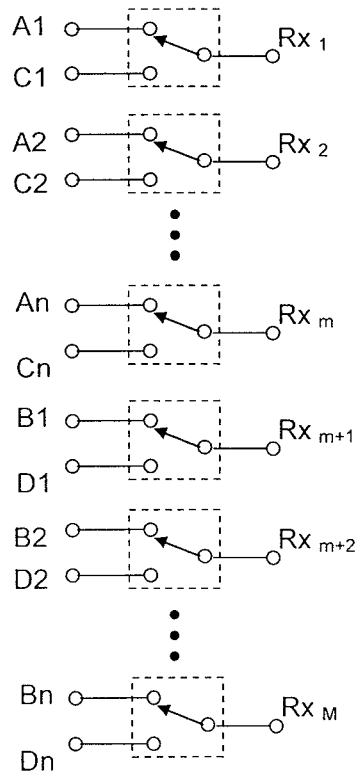
FIG. 6 is a drawing schematically illustrating a low-voltage multiplexer used in the ultrasound probe of embodiment 2.

On the other hand, as shown in FIG. 6, the low-voltage multiplexer 43 is a 2:1 multiplexer which selectively connects each of the receiving circuits Rx1-RxM to either of two ultrasound transducers. Of the M receiving circuits Rx1-RxM, half of them, the m receiving circuits Rx1-Rxm, are selectively connected to either one ultrasound transducer of group A or one ultrasound transducer of group C, and the remaining half of them, the m receiving circuits Rxm+1-RxM, are selectively connected to either one ultrasound transducer of group B or one ultrasound transducer of group D. For example, the 1st receiving circuit Rx1 is connected to either the 1st ultrasound transducer A1 of group A or the 1st ultrasound transducer C1 of group C, and the m+1th receiving circuit Rxm+1 is connected to either the 1st ultrasound transducer B1 of group B or the 1st ultrasound transducer D1 of group D.

Note that a switch means in the present invention is constructed from the high-voltage multiplexer 41, the low-voltage multiplexer 43 and the protection switch 46.

Next, the operation of embodiment 2 will be described. First, in the state where each protection switch 46 has been turned off by the controller 47, when analog high-voltage drive signals are sent from the apparatus body (not shown) via the signal wires S1-Sm of the connection cable 2, these drive signals are supplied to the respective ultrasound transducers 4 connected by the high-voltage multiplexer 41, and an ultrasonic beam is transmitted from those ultrasound transducers 4.

A reception signal output from the ultrasound transducer 4 which received an ultrasonic echo passes through the overvoltage protection circuit 42 and is input into the receiving circuit selected by the low-voltage multiplexer 43. The reception signal thus input is amplified by the preamp AMP and the variable gain amp VGA, removed of high-frequency components by the low pass filter LPF, converted to a digital signal by the A/D converter ADC, and then stored in the memory 44.

In this way, the reception signals that were amplified and A/D converted in the receiving circuits Rx1-RxM are stored in the memory 44.

Then, when an echo has been received from the deepest part of the subject, the reception of ultrasonic echoes ends, each switch of the protection switch 46 is turned on by the controller 47, and the digital reception signals stored in the memory 44 are collected and transferred to the apparatus body via the signal wires S1-Sm of the connection cable 2 by the digital calculator/digital output controller 45. That is, the analog drive signals and digital reception signals are mutually time-divided and sent via common signal wires S1-Sm. Transfer of reception signals to the apparatus body may be performed serially or in parallel.

When transfer of reception signals to the apparatus body is completed, transmission of ultrasonic waves and reception of ultrasonic echoes is similarly performed by the ultrasound transducers 4 whose connection has been switched by the high-voltage multiplexer 41 and the low-voltage multiplexer 43, and the reception signals stored in the memory 44 are collected and transferred to the apparatus body via the signal wires S1-Sm of the connection cable 2.

When reception signals have been input by all of the ultrasound transducers 4, the apparatus body generates an ultrasound image by processing those reception signals, and displays it on a display monitor or the like (not shown).

In embodiment 2, similar to embodiment 1, drive signals and reception signals can be sent using a number of signal wires S1-Sm which is less than the number N of ultrasound transducers 4.

For example, if the number N of ultrasound transducers 4 of the ultrasound probe is 128, the number m of signal wires of the connection cable 2 is 32 and the number M of receiving circuits is 64, then 64 channels of reception signals which were digitized by these receiving circuits can be converted to 32 channels by the digital calculator/digital output controller 45 with the so-called TSS method or compression, and sent to the apparatus body 3 through 32 signal wires. The reception signals, in the apparatus body 3, can be then returned to 64 channels and stored in the element data memory 25.

In addition, in cases where a maximum of only 32 channels of an ultrasound probe having 128 channels can be transmitted at once due to the use of an ultrasonic beam spread by the so-called zone method, the connection cable 2 can be made to have 16 channels by using an 8:1 multiplexer as the high-voltage multiplexer 41 that connects the ultrasound transducers 4 of the ultrasound probe and the connection cable 2. The reception signals digitized by the 64 receiving circuits are converted to 16 channels by the digital calculator/digital output controller 45 and then sent to the apparatus body using 16 signal wires, and in the apparatus body 3, the reception signals are returned to 64 channels by a 4:1 multiplexer, and can be stored in the element data memory 25.

However, if analog drive signals and digital reception signals can be mutually time-divided and sent by the signal wires of the connection cable 2 using a number m of signal wires that is less than the total number N of ultrasound transducers 4, then the total number N of ultrasound transducers 4, the number M of receiving circuits and the number m of signal wires of the connection cable 2 can be appropriately set.

In contrast, in a conventional ultrasound diagnostic apparatus, in the case where reception signals from a 128-channel ultrasound probe are received by 64 receiving circuits, for example, the reception signals are transferred from the ultrasound probe to the apparatus body by a 128-channel connection cable, and in the apparatus body, they have to be converted to 64 channels by a 2:1 multiplexer, or, a 2:1 multiplexer is built into the ultrasound probe, and the reception signals have to be sent from the ultrasound probe to 64 receiving circuits in the apparatus body by a 64-channel connection cable, and the number of signal wires of the connection cable cannot be greatly decreased as it is in the present invention.

Also, in embodiment 2, after reception signals from the ultrasound transducers are temporarily stored in the memory 44, all of the reception signals can be detected by the apparatus body without losing some of the reception signals, even if a general-purpose active switch is used as the protection switch 46 for collecting and transferring them to the apparatus body.

Note that as first-order processing, part of the focal point formation calculation may be performed on the reception signals stored in the memory 44 by the digital calculator/digital output controller 45, and then the reception signals may be transferred to the apparatus body. By so doing, the burden of signal processing in the apparatus body is reduced.

Embodiment 3

If a plurality of ultrasound transducers can be driven by one signal wire of the connection cable during one transmission period of ultrasonic waves, the number of signal wires in the connection cable can be reduced, and the weight of the connection cable can be reduced.

Figure 7:
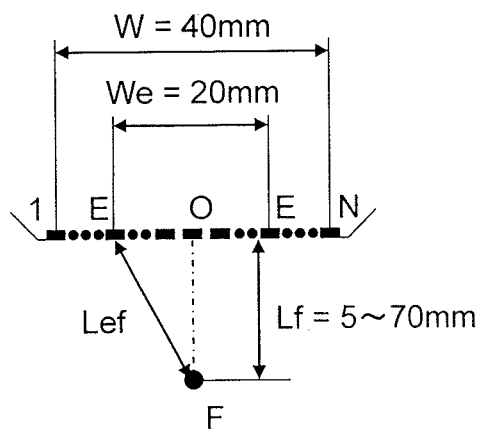
FIG. 7 is a drawing schematically illustrating an aperture of an ultrasound probe.

For example, as shown in FIG. 7, if an aperture width W of an ultrasound probe is 40 mm, a maximum transmission aperture width We is 20 mm, a transmission focal length Lf is 5-70 mm and the speed of sound c is taken as 1530 m/s, a delay time τ between a transmission aperture center O and a transmission aperture edge E when ultrasonic waves are transmitted from the ultrasound probe 1 in the forward direction is $$\tau=(Lef-Lf)/c$$

Figure 8:
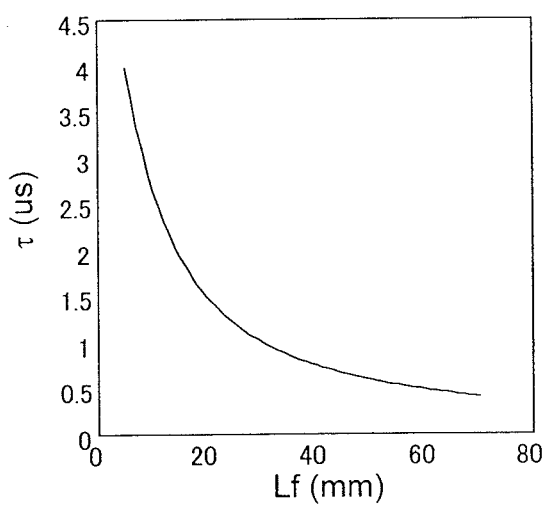
FIG. 8 is a graph illustrating a delay time between a center of a transmission aperture and an edge of a transmission aperture of an ultrasound probe.

Here, Lef indicates the distance between the focal point F and the transmission aperture edge E. FIG. 8 graphically shows the delay time τ as a function of transmission focal length Lf. The delay time τ corresponding to transmission focal length Lf=5-70 is about 4 µs or less.

In contrast, the response speed of a general-purpose high-voltage switch is 3-5 µs when turned on or off, and some of the reception signals are lost when an ultrasound transducer is switched by operating a high-voltage switch during one transmission period of ultrasonic waves.

Figure 9:
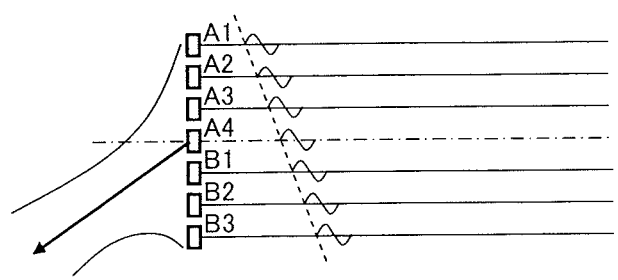
FIG. 9 is a drawing illustrating a method of driving ultrasound transducers in embodiment 3.

Here, in embodiment 3, ultrasonic beams can be transmitted in a tilted direction from the plurality of ultrasound transducers 4 arranged in an array, by mutually offsetting the timing of supply of drive signals to the plurality of ultrasound transducers 4, as shown in FIG. 9.

For example, for groups A-D of ultrasound transducers of the ultrasound probe used in embodiment 2 described above, immediately after an ultrasonic wave is transmitted from the 1st ultrasound transducer A1 of group A, an ultrasonic wave is transmitted from the 1st ultrasound transducer B1 of group B, and after that, ultrasonic waves are respectively transmitted from the 2nd ultrasound transducer A2 of group A, the 2nd ultrasound transducer B2 of group B, the 3rd ultrasound transducer A3 of group A, the 3rd ultrasound transducer B3 of group B, etc., by alternately switching among the n ultrasound transducers A1-An of group A and the n ultrasound transducers B1-Bn of group B.

Figure 10:
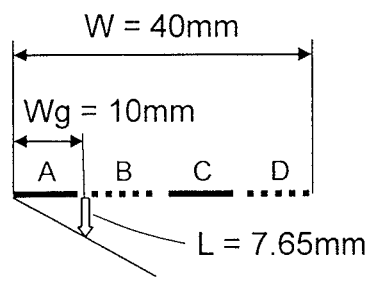
FIG. 10 is a drawing schematically illustrating an ultrasound probe in embodiment 3.

In this case, as shown in FIG. 10, since the aperture width W=40 mm of the ultrasound probe is divided into four groups, the aperture width Wg of each group is 10 mm, and if the response time of a general-purpose high-voltage switch is considered to be 5 µs, 5 µs is required for the general-purpose high-voltage switch to be switched and an ultrasonic wave to be transmitted from the 1st ultrasound transducer B1 of group B after an ultrasonic wave has been transmitted from the 1st ultrasound transducer A1 of group A, and during this time, the ultrasonic waves advance by length L=1530 (m/s)×5 (µs)= 7.65 (mm).

Figure 11:
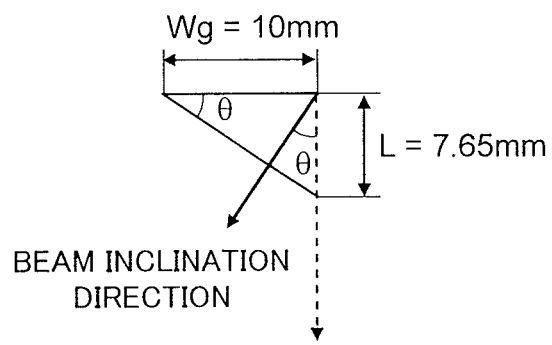
FIG. 11 is a drawing schematically illustrating a transmission beam inclination direction in embodiment 3.

For this reason, when the n ultrasound transducers A1-An of group A and the n ultrasound transducers B1-Bn of group B transmit ultrasonic waves alternately in sequence with a time gap of 5 µs, as shown in FIG. 11, an ultrasonic beam is transmitted at an incline in a direction tilted from the forward direction of the ultrasound probe by an angle represented by the following equation:

$$\theta=\tan^{-1}(L/Wg)=\tan^{-1}(7.65/10)=37.4°.$$

In doing so, by inclining the transmission direction of the ultrasonic beam from the plurality of ultrasound transducers, the plurality of ultrasound transducers can be driven using one signal wire of the connection cable, without losing some of the reception signals.

If an ultrasonic beam has been transmitted in a tilted direction in this way, reception RF signals of a period of at least 1 frame received by each ultrasound transducer, or signals equivalent to the reception RF signals such as those obtained by complex baseband conversion of the reception RF signals, are stored in the apparatus body, and by synthesizing signals on virtual scan lines which differ from the actual scan lines by adjacent reception signals in a plurality of directions, it is possible to generate an ultrasound image based on the virtual scan lines.

Specifically, by performing the 1st reception focusing process on a plurality of echo signals obtained by one transmission of ultrasonic beams, 1st sound ray data is generated and stored for a plurality of scan lines for each transmission of ultrasonic beams, and from these 1st sound ray data, the 1st sound ray data generated by transmitting ultrasonic beams in a plurality of directions is read, and the 2nd focusing process is performed on these, and one lines' worth of 2nd sound ray data is thereby generated. For example, the 2nd sound ray data is generated by performing the 2nd reception focusing process on the 1st sound ray data generated from the echoes of the nth transmitted ultrasonic beam and the 1st sound ray data generated from the echoes of the n+1th transmitted ultrasonic beam.

Figure 12:
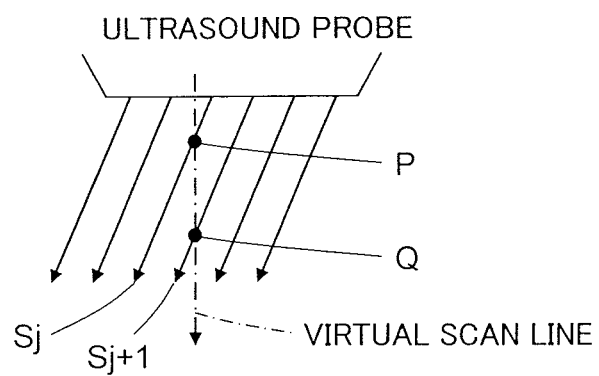
FIG. 12 is a drawing illustrating a method of creating an image in embodiment 3.

In this way, as shown in FIG. 12, for an echo from point P, for example, a reception RF signal due to ultrasonic wave Sj transmitted from the jth ultrasound transducer of the ultrasound probe is used, and for an echo from point Q, a reception RF signal due to ultrasonic wave Sj+1 transmitted from the j+1th ultrasound transducer of the ultrasound probe is used, and by synthesizing these reception RF signals, an ultrasound image can be generated based on virtual scan lines.

What is claimed is:

1. An ultrasound diagnostic apparatus comprising:
an ultrasound probe having a plurality of ultrasound transducers arranged in an array;
a diagnostic section which supplies analog drive signals to the plurality of ultrasound transducers of said ultrasound probe to transmit an ultrasonic beam toward a subject, and generates ultrasound images based on reception signals output from said plurality of ultrasound transducers which received ultrasonic echoes due to the subject; and
a connection cable which connects said ultrasound probe and said diagnostic section,
said ultrasound probe comprising:
a plurality of receiving circuits, each including a preamp which amplifies the reception signal output from one of said plurality of ultrasound transducers and an analogue/digital converter which converts the reception signal amplified by said preamp to a digital signal;
a plurality of transmission signal wires each arranged in parallel to each of said plurality of receiving circuits;
a plurality of first switches, which selectively connect one end of the corresponding receiving circuit and one end of the corresponding transmission signal wire to one of said plurality of ultrasound transducers;
a plurality of second switches, which selectively connect the other end of the corresponding receiving circuit and the other end of the corresponding transmission signal wire to said connection cable;
a plurality of element data memories which correspond to said plurality of receiving circuits, each of said plurality of element data memories temporarily storing said reception signal converted to a digital signal by a corresponding one of said plurality of receiving circuits; and
a controller which controls said plurality of first switches and said plurality of second switches to control output of said reception signal to said diagnostic section such that said drive signal supplied from said diagnostic section and said reception signal output to said diagnostic section after being converted to digital signal by each of said plurality of receiving circuits are mutually time-divided and sent via said connection cable,
when each of said plurality of receiving circuits is connected to said connection cable by a corresponding one of said plurality of second switches, said reception signal having been temporarily stored in a corresponding one of said plurality of memories is sent to said diagnostic section via said connection cable.

2. The ultrasound diagnostic apparatus according to claim 1, wherein said connection cable is made up of signal wires of a number less than the number of said ultrasound transducers of said ultrasound probe.

3. The ultrasound diagnostic apparatus according to claim 1, wherein each of said plurality of first switches is a passive switch which automatically operates based on a potential of the corresponding transmission signal wire, and each of said plurality of second switches is an active switch which operates based on a control signal input from said controller.

4. An ultrasound diagnostic apparatus comprising:
an ultrasound probe having a plurality of ultrasound transducers arranged in an array;
a diagnostic section which supplies analog drive signals to the plurality of ultrasound transducers of said ultrasound probe to transmit an ultrasonic beam toward a subject, and generates ultrasound images based on reception signals output from said plurality of ultrasound transducers which received ultrasonic echoes due to the subject; and
a connection cable which connects said ultrasound probe and said diagnostic section, said connection cable being made up of signal wires of a number less than the number of said ultrasound transducers of said ultrasound probe,
said ultrasound probe comprising:
a plurality of receiving circuits, each including a preamp which amplifies the reception signal output from one of said plurality of ultrasound transducers and an analogue/digital converter which converts the reception signal amplified by said preamp to a digital signal;
a high-voltage multiplexer which selectively connects the plurality of signal wires of said connection cable and said plurality of ultrasound transducers;
a low-voltage multiplexer which selectively connects said plurality of ultrasound transducers and said plurality of receiving circuits, and
a controller which controls said high-voltage multiplexer and said low-voltage multiplexer such that said drive signal supplied from said diagnostic section and said reception signal output to said diagnostic section after being converted to digital signal by each of said plurality of receiving circuits are mutually time-divided and sent via said connection cable.

5. The ultrasound diagnostic apparatus according to claim 4, wherein said diagnostic section drives said plurality of ultrasound transducers by supplying a plurality of drive signals supplied during one transmission period via each signal wire of said connection cable.

6. The ultrasound diagnostic apparatus according to claim 5, wherein said diagnostic section drives offsets mutually the timing of supply of said drive signals to said plurality of ultrasound transducers to tilt a transmission direction of the ultrasonic beams from said plurality of ultrasound transducers.

7. The ultrasound diagnostic apparatus according to claim 6, wherein said diagnostic section reception RF signals of a period of at least one frame received by said plurality of ultrasound transducers and sent from said ultrasound probe via said connection cable or signals equivalent to the reception RF signals, and generates an ultrasound image based on virtual scan lines, by synthesizing signals on the virtual scan lines which differ from actual scan lines, with using adjacent reception signals in a plurality of directions.

* * * * *